United States Patent
Magnuson

(10) Patent No.: US 6,924,419 B2
(45) Date of Patent: Aug. 2, 2005

(54) GARDEN BEAN NAMED '211945'

(75) Inventor: D. Stephen Magnuson, Lehigh Acres, FL (US)

(73) Assignee: Harris Moran Seed Company, Modesto, CA (US)

( * ) Notice: Subject to any disclaimer, the term of this patent is extended or adjusted under 35 U.S.C. 154(b) by 5 days.

(21) Appl. No.: 10/357,952

(22) Filed: Feb. 4, 2003

(65) Prior Publication Data

US 2004/0154058 A1 Aug. 5, 2004

(51) Int. Cl.⁷ .............................. A01H 1/00; A01H 4/00; A01H 5/00; A01H 5/10; C12N 15/82

(52) U.S. Cl. ....................... 800/313; 435/410; 800/260; 800/278; 800/298; 800/300; 800/301; 800/302

(58) Field of Search .......................... 435/410; 800/260, 800/266, 298, 300, 313, 301, 302

(56) References Cited

PUBLICATIONS

Darnell et al 1990, In Molecular Cell Biology, Scientific American Books, Inc. New York, New York, p. 478.*
Bassett et al 1999, J. Amer. Soc. Hort. Sci. 124(6): 649–653.*
Allard, R.W., 1960, Selection Under Self–Fertilization, In Principles of Plant Breeding, John Wiley & Sons, Inc., pp. 155–156.

* cited by examiner

*Primary Examiner*—David H Kruse
(74) *Attorney, Agent, or Firm*—Jondle & Associates P.C.

(57) ABSTRACT

A novel garden bean cultivar, designated '211945', is disclosed. The invention relates to the seeds of garden bean cultivar '211945', to the plants of garden bean line '211945' and to methods for producing a bean plant by crossing the cultivar '211945' with itself or another bean line. The invention further relates to methods for producing a bean plant containing in its genetic material one or more transgenes and to the transgenic plants produced by that method and to methods for producing other garden bean lines derived from the cultivar '211945'.

16 Claims, No Drawings

GARDEN BEAN NAMED '211945'

BACKGROUND OF THE INVENTION

The present invention relates to a new and distinctive Garden Bean (*Phaseolus vulgaris*) variety, designated '211945'. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include fresh pod yield, higher seed yield, resistance to diseases and insects, better stems and roots, tolerance to drought and heat, and better agronomic quality. With mechanical harvesting of many crops, uniformity of plants characteristics such as germination and stand establishment, growth rate, maturity and plant height is important.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior garden bean cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same bean traits.

Each year, the plant breeder selects the germplasm to advance to the next generation. This germplasm is grown under unique and different geographical, climatic and soil conditions, and further selections are then made, during and at the end of the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior garden bean cultivars.

The development of commercial garden bean cultivars requires the development of garden bean varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the progeny from these crosses are evaluated to determine which have commercial potential as a new variety.

Pedigree breeding is used commonly for the improvement of self-pollinating crops or inbred lines of cross-pollinating crops. Two parents that possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed Descriptions of other breeding methods that are commonly used for different traits and crops can be found in one of several reference books (e.g., "Principles of Plant Breeding" John Wiley and Son, pp. 115–161, 1960; Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Garden bean, *Phaseolus vulgaris* L., is an important and valuable vegetable crop. Thus, a continuing goal of plant breeders is to develop stable, high yielding garden bean cultivars that are agronomically sound. The reasons for this goal are obviously to maximize the amount of yield produced on the land. To accomplish this goal, the garden bean breeder must select and develop garden bean plants that have the traits that result in superior cultivars.

SUMMARY OF THE INVENTION

According to the invention, there is provided a novel garden bean cultivar, designated '211945'. This invention thus relates to the seeds of garden bean cultivar '211945', to the plants of garden bean cultivar '211945' and to methods for producing a garden bean plant produced by crossing the garden bean '211945' with itself or another garden bean line, and to methods for producing a garden bean plant containing in its genetic material one or more transgenes and to the transgenic garden bean plants produced by that method. This invention also relates to methods for producing other garden bean cultivars derived from garden bean cultivar '211945' and to the garden bean cultivar derived by the use of those methods. This invention further relates to hybrid garden bean seeds and plants produced by crossing the line '211945' with another garden bean line.

In another aspect, the present invention provides regenerable cells for use in tissue culture of garden bean cultivar '211945'. The tissue culture will preferably be capable of regenerating plants having the physiological and morphological characteristics of the foregoing garden bean plant, and of regenerating plants having substantially the same genotype as the foregoing garden bean plant. Preferably, the regenerable cells in such tissue cultures will be embryos, protoplasts, seeds, callus, pollen, leaves, anthers, roots, and meristematic cells. Still further, the present invention provides garden bean plants regenerated from the tissue cultures of the invention.

Another objective of the invention is to provide methods for producing other garden bean plants derived from garden bean cultivar '211945'. Garden bean cultivars derived by the use of those methods are also part of the invention.

The invention also relates to methods for producing a garden bean plant containing in its genetic material one or more transgenes and to the transgenic garden bean plant produced by that method.

In another aspect, the present invention provides for single gene converted plants of '211945'. The single transferred gene may preferably be a dominant or recessive allele. Preferably, the single transferred gene will confer such trait as male sterility, herbicide resistance, insect resistance, resistance for bacterial, fungal, or viral disease, male fertility, enhanced nutritional quality and industrial usage. The single gene may be a naturally occurring bean gene or a transgene introduced through genetic engineering techniques.

The invention further provides methods for developing a bean plant in a bean plant breeding program using plant breeding technique including recurrent selection, backcrossing, pedigree breeding, restriction fragment length polymorphism enhanced selection, genetic marker enhanced selection and transformation. Seeds, bean plant, and parties thereof produced by such breeding methods are also part of the invention.

DEFINITIONS

In the description and tables which follow, a number of terms are used. In order to provide a clear and consistent understanding of the specification and claims, including the scope to be given such terms, the following definitions are provided:

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Essentially all the physiological and morphological characteristics. A plant having essentially all the physiological and morphological characteristics means a plant having the physiological and morphological characteristics, except for the characteristics derived from the converted gene.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of a line are recovered in addition to the single gene transferred into the line via the backcrossing technique or via genetic engineering.

Maturity Date. Plants are considered mature when the pods have reached their maximum allowable seed size and sieve size for the specific use intended. This can vary for each end user, e.g., processing at different stages of maturity would be required for different types of consumer beans such as "whole pack," "cut" or "french style". The number of days are calculated from a relative planting date which depends on day length, heat units and environmental other factors.

Maturity. A maturity under 53 days is considered early while one between 54–59 days would be considered average or medium and one of 60 or more days would be late.

Sieve Size (sv). Sieve size 1 means pods that fall through a sieve grader which culls out pod diameters of 4.76 mm through 5.76 mm. Sieve size 2 means pods that fall through a sieve grader which culls out pod diameters of 5.76 mm through 7.34 mm. Sieve size 3 means pods that fall through a sieve grader which culls out pod diameters of 7.34 mm through 8.34 mm. Sieve size 4 means pods that fall through a sieve grader which culls out pod diameters of 8.34 mm through 9.53 mm. Sieve size 5 means pods that fall through a sieve grader which culls out pod diameters of 9.53 mm through 10.72 mm. Sieve size 6 means pods that fall through a sieve grader that will cull out pod diameters of 10.72 mm or larger.

Bean Yield (Tons/Acre). The yield in tons/acre is the actual yield of the bean pods at harvest.

Plant Height. Plant height is taken from the top of soil to top node of the plant and is measured in centimeters.

Field holding ability. A bean plant that has field holding ability means a plant having pods those remain smooth and retain their color even after the seed is almost fully developed.

Machine harvestable hush. A machine harvestable bush means a bean plant that stands with pods off the ground. The pods can be removed by a machine from the plant without leaves and other plant parts.

Plant adaptability. A plant having a good plant adaptability means a plant that will perform well in different growing conditions and seasons.

Emergence. Emergence is the rate that the seed germinates and sprouts out of the ground.

Plant architecture. Plant architecture is the shape of the overall plant which can be tall-narrow, short-wide, medium height, medium width.

Determinate Plant: a determinate plant will grow to a fixed number of nodes while an indeterminate plant continues to grow in length and produce pods during the season.

Plant habit. A plant can be erect (upright) to sprawling on the ground.

Pod set height. The pod set height is the location of the pods within the plant. The pods can be high (near the top), low (near the bottom), or medium (in the middle) of the plant.

Concentrated set of pods: a concentrated set of pods is said of a plant where all pods mature in a short period of time (e.g. 2 to 3 days).

Heat tolerance. Heat tolerance is the ability to produce pods under conditions of 75 and over degrees F during the night and 90 and over degrees F during daytime.

RHS. RHS refers to the Royal Horticultural Society of England which publishes an official botanical color chart quantitatively identifying colors according to a defined numbering system, The chart may be purchased from Royal Hort Society Enterprise Ltd RHS Garden; Wisley, Woking; Surrey GU236QB, UK.

Resistance to a disease: a bean plant is said to be resistant to a disease when neither the plant nor the pods show any symptoms of the disease and when the yield is not affected.

Tolerance to a disease: a bean plant being tolerant to a disease can still produce when exposed to the disease but yields may be lowered and leaves and pods may show symptoms.

DETAILED DESCRIPTION OF THE INVENTION

Garden bean cultivar '211945' has superior characteristics and was developed from the intial cross that was made in the San Juan Bautista, Calif., Harris Moran Seed Company research station greenhouse in November, 1996 between two proprietary lines under stake numbers M2368 (female) and M2071 (male). The F1 generation was grown in the greenhouse during the spring of 1997 under the stake number M2X428. The F2 selection was made on Aug. 25, 1997, in Texas, selection number three (3) of three selections. The F3 selection was made on Feb. 25, 1998 in the Harris Moran Seed Company research grounds near Los Mochis, Mexico in plot 4N0794, selection number two (2) of four selections. The F4 selection was made on Jul. 18, 1998 on the Robert Heath Farm, Coloma, Wis. in plot number 4Y3638, selection number one (1) of five selections. The F5 generation was bulked in plot 5M0213 on Feb. 9, 1999 in the Harris Moran Seed Company research grounds near Los Mochis, Mexico for initial observation. The F6 selection was made on Jul. 21, 1999 in plot 99WA107, selection number one (1) of two selections. The F7 generation was bulked in Mexico in February, 2000, under plot numbers 6L350, 6L351, and 6L352 and carried as breeder line 99107.

The cultivar '211945' is most similar to the variety 'HM 5991'. '211945' is resistant to Bacterial Brown Spot and HM 5991 is susceptible. 211945 is 2 days earlier than HM 5991 and has a more concentrated set of pods, the pods of 211945 being all mature in a 2 to 3 days period, the pods of 'HM 5991' being all mature in a 7 to 10 days period. The plant habit of '211945' stands erect and is narrower than HM 5991.

'211945' is an average maturity (58 days) snap bean with a dark green color (from 147A to 147B on the RHS color chart), straight, smooth pods. '211945' has an erect plant structure with the pods in the middle to the top of the plant. '211945' is a determinate plant. '211945' has heat tolerance and is resistant to Bacterial Brown Spot Bean Common Mosaic Virus and Beet Curly Top Virus.

Some of the criteria used to select in various generations include: pod appearance and length, bean yield, pod set height, emergence, maturity, plant architecture, habit and height, seed yield and quality, and disease resistance.

Bean common mosaic virus resistance is a desired trait for a bean variety. The disease occurs worldwide causing low quality of the harvest product and losses from 80 to 100% by reduction of yield. It is mostly transmitted by aphids during the growing season, but can also be spread by pollen or mechanically. Leaves develop mosaic patterns in which irregular light and dark green patch are intermixed. Malformation and yellow dots may also be produced, often causing growth reduction. The plant may be dwarfed and pod and seed yield reduced. Severe necrosis may occur and the plant may die if infected while young. Systemic necrosis, in which the roots and shoots become blackened, appears in cultivar having dominant resistance gene/(hypersensitive resistance mechanism). The systemic necrosis may spread to higher leaves without killing them or may be concentrated in the vascular parts of the stem, eventually leading to the death of all or part of the plant. When infection occurs late in plant development, parts of the plant may die and many pods may show brown discoloration in the pod wall and pod suture as a result of vascular necrosis.

Bacterial Brown Spot is a bacterial disease that can severely damage bean fields. Brown Spot is caused by *Pseudomonas syringae* pv. syringae. The plant may suffers multiple lesion, on leafs (circular, brown and necrotic) but also on stem and pods.

The sugar beet curly top virus is a viral disease due to a geminivirus transmitted by leafhoppers. Many strains have bean reported. Symptoms on the plants vary greatly due to a wide range of sensitivity, but are mainly yellowing type (leafs turn yellow and the plant dies). The disease is mostly present in arid and semiarid regions of western North America, Mediterranean region, Iran and India.

The cultivar has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in '211945'.

Garden bean cultivar '211945' has the following morphologic and other characteristics (based primarily on data collected at Sun Prairie, Wis. Research Station).

VARIETY DESCRIPTION INFORMATION

Market Maturity
Days to edible pods: 58 days.
Number of days earlier than 'HM 5991':02 days
Plant
Habit: Determinate
Plant:
Height: 40 cm
Same height as 'HM 5991'
Spread: 30 cm
Narrower than 'HM 5991' by 10 cm
Pod position: Middle to top of plant
Bush Form: High bush form
Leaves
Surface: Glossy
Size: Small
Color: Dark Green
Anthocyanin Pigment
Flowers: Absent
Stems: Absent
Pods: Absent
Seeds: Absent
Leaves: Absent
Petioles: Absent
Peduncles: Absent
Nodes: Absent
Flower Color
Color of standard: White
Color of keel: White
Pods (edible maturity)
Exterior color: Dark Green
Processed pods: Dark
Dry pod color: Buckskin
Cross Section Pod shape: Round
Creaseback: Present
Pubescence: Sparse
Constriction: Slight
Spur length: 10 mm
Fiber: Sparse
Number seeds/pod: 6
Suture string: Absent
Seed development: Fast
Machine harvest: Adapted
Distribution of sieve size at optimum maturity:
% 4.76–5.76 mm-Sieve 1
% 5.76–7.34 mm-Sieve 2
40% 7.34–8.34 mm-Sieve 3
60% 8.34–9.53 mm-Sieve 4
Average Length of 3 sieve: 13.5 cm
Average Length of 4 sieve: 14.0 cm
Seed Color
Seed coat: Monochrome
Primary color: white
Seedcoat Pattern: Solid
Hilar ring: Absent
Disease Resistance
Bean Common Mosaic Virus (BCMV)
Beet Curly Top Virus (BCTV)
Bacterial Brown Spot

FURTHER EMBODIMENTS OF THE INVENTION

This invention also is directed to methods for producing a garden plant by crossing a first parent bean plant with a second parent bean plant wherein either the first or second parent bean plant is an bean plant of the line '211945'. Further, both first and second parent bean plants can come from the cultivar '211945'. Still further, this invention also is directed to methods for producing a cultivar '211945'-derived bean plant by crossing cultivar '211945' with a second bean plant and growing the progeny seed, and repeating the crossing and growing steps with the cultivar '211945'-derived plant from 0 to 7 times. Thus, any such methods using the cultivar '211945' are part of this invention: selfing, backcrosses, hybrid production, crosses to populations, and the like. All plants produced using cultivar '211945' as a parent are within the scope of this invention, including plants derived from cultivar '211945'. Advantageously, the cultivar is used in crosses with other, different, cultivars to produce first generation ($F_1$) bean seeds and plants with superior characteristics.

As used herein, the term plant includes plant cells, plant protoplasts, plant cell tissue cultures from which garden bean plants can be regenerated, plant calli, plant clumps and plant cells that are intact in plants or parts of plants, such as embryos, pollen, ovules, flowers, seeds, pods, stems, roots, anthers, and the like.

As is well known in the art, tissue culture of garden bean can be used for the in vitro regeneration of a garden bean plant. Tissue culture of various tissues of garden beans and regeneration of plants therefrom is well known and widely published. For example, reference may be had to McClean, P.; Grafton, K. F. (1989): "Regeneration of dry bean (*Phaseolus vulgaris*) via organogenesis." *Plant Sci.* 60,117–122. Mergeai, G.; Baudoin, J. P. (1990): "Development of an in vitro culture method for heart-shaped embryo in *Phaseolus vulgaris.*" B.I.C. Invit. Papers 33, 115–116. Vanderwesthuizen, A. J.; Groenewald, E. G. (1990): "Root Formation and Attempts to Establish Morphogenesis in Callus Tissues of Beans (*Phaseolus-Vulgaris* L.)." *S. Afr. J. Bot.* 56(2, April), 271–273. Benedicic, D., et al. (1990): "The regeneration of *Phaseolus vulgaris* L. plants from meristem culture." Abst. 5th I.A.P.T.C. Cong. 1, 91 (#A3–33). Genga, A.; Allavena, A. (1990): "Factors affecting morphogenesis from immature cotyledons of *Phaseolus coccineus* L." Abst. 5th I.A.P.T.C. Cong. 1,101 (#A3–75). Vaquero, F., et al. (1990): "Plant regeneration and preliminary studies on transformation of *Phaseolus coccineus.*" Abst. 5th I.A.P.T.C. Cong. 1, 106 (#A3–93). Franklin, C. I., et al. (1991): "Plant Regeneration from Seedling Explants of Green Bean (*Phaseolus-Vulgaris* L.) via Organogenesis." *Plant Cell Tissue Org. Cult.* 24(3, March), 199–206. Malik, K. A.; Saxena, P. K. (1991): "Regeneration in *Phaseolus-Vulgaris* L.—Promotive Role of N6-Benzylaminopurine in Cultures from Juvenile Leaves." *Planta* 184(1), 148–150. Genga, A.; Allavena, A. (1991): "Factors affecting morphogenesis from immature cotyledones of *Phaseolus coccineus* L." *Plant Cell Tissue Org. Cult.* 27, 189–196. Malik, K. A.; Saxena, P. K. (1992): "Regeneration in *Phaseolus vulgaris* L. L.—High-Frequency Induction of Direct Shoot Formation in Intact Seedlings by N-6-Benzylaminopurine and Thidiazuron." 186 (3, Feb.), 384–389. Malik, K. A.; Saxena, P. K. (1992): "Somatic Embryogenesis and Shoot Regeneration from Intact Seedlings of *Phaseolus acutifolius* A., *P. aureus* (L.) Wilczek, *P. coccineus* L., and *P. wrightii* L." *Pl. Cell. Rep.* 11 (3, April), 163–168. Chavez, J., et al. (1992): "Development of an in vitro culture method for heart shaped embryo in *Phaseolus polyanthus.*" B.I.C. Invit. Papers 35, 215–216. Munoz-Florez, L.C., et al. (1992): "Finding out an efficient technique for inducing callus from Phaseolus microspores." B.I.C. Invit. Papers 35, 217–218. Vaquero, F., et al. (1993): "A Method for Long-Term Micropropagation of *Phaseolus coccineus* L." *L. Pl. Cell. Rep.* 12 (7–8, May), 395–398. Lewis, M. E.; Bliss, F. A. (1994): "Tumor Formation and beta-Glucuronidase Expression in *Phaseolus vulgaris* L. Inoculated with *Agrobacterium Tumefaciens.*" Journal of the American Society for *Horticultural Science* 119(2, March), 361–366. Song, J. Y., et al. (1995): "Effect of auxin on expression of the isopentenyl transferase gene (ipt) in transformed bean (*Phaseolus vulgaris* L. L.) single-cell clones induced by *Agrobacterium tumefaciens* C58." *J. Plant Physiol.* 146 (1–2, May), 148–154. It is clear from the literature that the state of the art is such that these methods of obtaining plants are, and were, "conventional" in the sense that they are routinely used and have a very high rate of success. Thus, another aspect of this invention is to provide cells which upon growth and differentiation produce bean plants having the physiological and morphological characteristics of variety '211945'.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed bean plants, using transformation methods as described below to incorporate transgenes into the genetic material of the bean plant(s).

Expression Vectors for Bean Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80:4803 (1983), Aragao F. J. L., et al., *Molecular Breeding* 4:6 491–499 (1998). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990), Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988), Saker M. M., et al, *Biologia Plantarum* 40:4 507–514 (1998), Russel, D. R., et al, *Plant Cell Report* 12:3 165–169 (1993).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), alpha-galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984), Grossi M. F., et al., *Plant Science* 103:2 189–198 (1994), Lewis M. E., *Journal of the American Society for Horticultural Science* 119:2 361–366 (1994), Zhang et al., *Journal of the American Society for Horticultural Science* 122:3 300–305 (1997).

Recently, in vivo methods for visualizing GUS activity that do not require destruction of plant tissue have been made available. Molecular Probes publication 2908, Imagene Green™, p. 1–4 (1993) and Naleway et al., *J. Cell Biol.* 115:151 a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in bean. Optionally, the inducible promoter is operably linked to a nucleotide sequence encoding a signal sequence which is operably linked to a gene for expression in bean. With an inducible promoter the rate of transcription increases in response to an inducing agent.

Any inducible promoter can be used in the instant invention. See Ward et al., *Plant Mol. Biol.* 22:361–366 (1993). Exemplary inducible promoters include, but are not limited to, that from the ACEI system which responds to copper (Meft et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) or Tet repressor from Tn10 (Gatz et al., *Mol. Gen. Genetics* 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in bean or the constitutive promoter is operably linked to a nucleotide sequence encoding a signal sequence which is operably linked to a gene for expression in bean.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985), Aragao et al., *Genetics and Molecular Biology* 22:3, 445–449 (1999) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter, Xba1/Ncol fragment 5' to the *Brassica napus* ALS3 structural gene (or a nucleotide sequence similarity to said Xba1/Ncol fragment), represents a particularly useful constitutive promoter. See PCT application WO96/30530.

C. Tissue-Specific or Tissue-Preferred Promoters

A tissue-specific promoter is operably linked to a gene for expression in bean. Optionally, the tissue-specific promoter is operably linked to a nucleotide sequence encoding a signal sequence which is operably linked to a gene for expression in bean. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476–482 (1983) and Sengupta-Gopalan et al., *Proc. Natl. Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217:240–245 (1989)); a pollen-specific promoter such as that from Zm13 (Guerrero et al., *Mol. Gen Genetics* 244:161–168 (1993)) or a microspore-preferred promoter such as that from apg (Twell et al., *Sex. Plant Reprod.* 6:217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3–17 (1987), Lerner et al., *Plant Physiol.* 91:124–129 (1989), Fontes et al., *Plant Cell* 3:483–496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is bean. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt delta-endotoxin gene. Moreover, DNA molecules encoding delta-endotoxin genes can be purchased from American Type Culture Collection, Manassas, Va., for example, under ATCC Accession Nos. 40098, 67136, 31995 and 31998.

C. A lectin. See, for example, the disclose by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See,for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cONA encoding tobacco proteinase inhibitor I), Sumitani et al., *Biosci. Biotech. Biochem.* 57:1243 (1993) (nucleotide sequence of *Streptomyces nitrosporeus* alpha-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in Diploptera puntata). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-beta, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo alpha-1,4-D-polypalacturonases facilitate fungal colonization and plant nutrient release by solubilizing plant cell wall alpha-1,4-D-gialacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A development-arrestive protein produced in nature by a plant. For example, Logemann et al., *Bioi/Technology* 10:305 (1992), have shown that transgenic plants expressing the barley ribosome-inactivating gene have an increased resistance to fungal disease.

2. Genes That Confer Resistance to a Herbicide, For Example:

A. A herbicide that inhibits the growing point or meristem, such as an imidazalinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. See also Russel, D. R., et al, *Plant Cell Report* 12:3 165–169 (1993). The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., *Theor. Appl. Genet.* 83:435 (1992).

C. A herbicide that inhibits photosynthesis, such as a triazine (psbA and gs+ genes) and a benzonitrile (nitrilase gene). Przibilla et al., *Plant Cell* 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes That Confer or Contribute to a Value-Added Trait, Such as:

A. Delayed and attenuated symptoms to Bean Golden Mosaic Geminivirus (BGMV), for example by transforming a plant with antisense genes from the Brazilian BGMV. See Arago et al., *Molecular Breeding*. 1998,4:6,491–499.

B. Increased the bean content in Methionine by introducing a transgene coding for a Methionine rich storage albumin (2S-albumin) from the Brazil nut as decribed in Arago et al., *Genetics and Molecular Biology*. 1999, 22:3, 445–449.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89–119.

A. Agrobacterium-Mediated Transformation

One method for introducing an expression vector into plants is based on the natural transformation system of Agrobacterium. See, for example, Horsch et al., *Science* 227:1229 (1985). McClean, P., et al. *Plant Cell Tissue Org. Cult.* 24(2, Feb.), 131–138 (1991), Lewis et al., *Journal of the American Society for Horticultural Science* 119:2, 361–366 (1994), Zhang, Z., et al. *J. Amer. Soc. Hort. Sci.* 122(3): 300–305 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of Agrobacterium vector systems and methods for Agrobacterium-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer

Despite the fact the host range for Agrobacterium-mediated transformation is broad, some major cereal or vegetable crop species and gymnosperms have generally been recalcitrant to this mode of gene transfer, even though some success has recently been achieved in rice and corn. Hiei et al., *The Plant Journal* 6:271–282 (1994) and U.S. Pat. No. 5,591,616 issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 im. The expression vector is introduced into plant tissues with a biolistic device that accelerates the microprojectiles to speeds of 300 to 600 m/s which is sufficient to penetrate plant cell walls and membranes. Russell, D. R., et al. *Pl. Cell. Rep.* 12(3, Jan.), 165–169 (1993), Aragao, F. J. L., et al. *Plant Mol. Biol.* 20(2, Oct.), 357–359(1992), Aragao *Theor. Appl. Genet.* 93:142–150 (1996), Kim, J.; Minamikawa, T. *Plant Science* 117: 131–138 (1996), Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992)

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-omithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Saker, M.; Kuhne, T. *Biologia Plantarum* 40(4): 507–514 (1997/98), Donn et al., In Abstracts of VIIth International Congress on Plant Cell and Tissue Culture IAPTC, A2–38, p 53 (1990); D'Halluin et al., *Plant Cell* 4:1495–1505 (1992) and Spencer et al., *Plant Mol. Biol.* 24:51–61 (1994).

Following transformation of bean target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic bean line. Alternatively, a genetic trait which has been engineered into a particular bean cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term garden bean plant, cultivar or bean line are used in the context of the present invention, this also includes any single gene conversions of that line. The term single gene converted plant as used herein refers to those garden bean plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term backcrossing as used herein refers to the repeated crossing of a hybrid progeny back to one of the parental bean plants for that line. The parental bean plant which contributes the gene for the desired characteristic is termed the nonrecurrent or donor parent. This terminology refers to the fact that the nonrecurrent parent is used one time in the backcross protocol and therefore does not recur. The parental bean plant to which the gene or genes from the nonrecurrent parent are transferred is known as the recurrent parent as it is used for several rounds in the backcrossing protocol (Poehiman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a garden bean plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, herbicide resistance (such as bar or pat genes), resistance for bacterial, fungal, or viral disease such as gene I used for BCMV resistance), insect resistance, enhanced nutritional quality (such as 2s albumine gene), industrial usage, agronomic qualities such as the "persistent green gene", yield stability and yield enhancement. These genes are generally inherited through the nucleus. Some other single gene traits are described in U.S. Pat. Nos. 5,777,196; 5,948,957 and 5,969,212, the disclosures of which are specifically hereby incorporated by reference.

Tables

In Tables 1 to 4 that follows, the traits and characteristics of garden bean line '211945' are given along with data on commercial garden bean lines used as checks.
Table 1: Plant characteristics, data collected in 2001 in several locations.
The first column lists the variety tested.
The second column shows the location.
Column 3 shows the plant height in inches.
Column 4 shows the plant width in inches.
Column 5 shows the plants habit on a scale from 1 to 5, with 1 being prone, 3 being moderate, 4 being upright and 5 being erect.

TABLE 1

Overall Comparisons: Plant characteristics
Garden Bean named '211945' vs Checks Year: 2001

| Variety | Location | Plant Height | Plant width | Plant Habit |
|---|---|---|---|---|
| FM658 | Havana (IL) | 16 | 18 | 3 |
| Labrador | Havana (IL) | 15 | 18 | 3 |
| 211945 | Havana (IL) | 15 | 14 | 5 |
| Minuette | Havana (IL) | 16 | 16 | 4 |
| FM658 | Heath Sales (WI) | 17 | 22 | 4 |
| Minuette | Heath Sales (WI) | 17 | 22 | 4 |
| Labrador | Heath Sales (WI) | 18 | 21 | 4 |
| 211945 | Heath Sales (WI) | 12 | 17 | 5 |
| 211945 | Heath Sales 2 (WI) | 18 | 18 | 5 |
| FM658 | Heath Sales 2 (WI) | 17 | 20 | 4 |
| Labrador | Heath Sales 2 (WI) | 18 | 21 | 4 |
| Minuette | Kramer's | 21 | 22 | 3.5 |
| 211945 | Kramer's | 24 | 22 | 4.5 |
| Labrador | LeRoy (NY) | 20 | 23 | 3.5 |
| Minuette | LeRoy (NY) | 19 | 21 | 4 |
| FM658 | LeRoy (NY) | 17 | 22 | 3 |
| 211945 | LeRoy (NY) | 18 | 19 | 4 |
| 211945 | New Richmond (WI) | 20 | 26 | 4 |
| Minuette | New Richmond (WI) | 18 | 28 | 3 |
| FM658 | New Richmond (WI) | 21 | 34 | 2 |
| Labrador | New Richmond (WI) | 20 | 34 | 2 |
| 211945 | Salem (OR) | 15 | 13 | |
| Minuette | Salem (OR) | 17 | 15 | 3.5 |
| Labrador | Sun Prairie (WI) | 18 | 19 | 4 |
| 211945 | Sun Prairie (WI) | 14.5 | 13 | 4.5 |
| FM658 | Sun Prairie (WI) | 17 | 16 | 3.5 |
| 211945 | Sun Prairie (WI) | 13 | 16 | 4 |
| Labrador | Sun Prairie (WI) | 16.5 | 18.5 | 3.5 |
| FM658 | Sun Prairie (WI) | 15.5 | 15.5 | 3.5 |
| Minuette | Sun Prairie (WI) | 13 | 12 | 3.5 |
| Minuette | Sun Prairie (WI) | 15.5 | 15.5 | 3.5 |
| 211945 | Texas | 17 | 17 | 3 |
| Labrador | Texas | 18 | 18 | 3 |
| FM658 | Texas | 21 | 24 | 2.5 |

Table 2: Pod characteristics, data collected in 2001 in several locations.
The first column lists the variety tested.
The second column shows the location.
Column 3 shows the pods position on a scale from 1 to 5 with 1 being all pods on ground, 3 being pods just off the ground and 5 being pods high off the ground.
Column 4 shows the pods length in centimeters.
Column 5 shows the pod color on a scale from 1 to 5, 1 being lightly colored, 3 being medium, and 5 being dark.
Column 6 shows the maturity (optimum maturity in days)
Column 7 shows the yield in net pounds per 5 feet.

TABLE 2

Overall Comparisons: Pod Characteristics
Garden Bean named '211945' vs Checks Year: 2001

| Variety | Location | Pod Position | Pod Length | Pod Color | Maturity | Yield |
|---|---|---|---|---|---|---|
| FM658 | Havana (IL) | 4 | 12.7 | 4 | 63 | 2.5 |
| Labrador | Havana (IL) | 3 | 10.8 | 4 | 62 | 1.37 |
| 211945 | Havana (IL) | 2.5 | 12.7 | 4 | 63 | 2.93 |
| Minuette | Havana (IL) | 3 | 10 | 4 | 63 | 2.81 |
| FM658 | Heath Sales (WI) | 2.5 | 13 | 3 | 56 | 2.94 |
| Minuette | Heath Sales (WI) | 3 | 11 | 4 | 60 | 3.07 |
| Labrador | Heath Sales (WI) | 3 | 12 | 3 | 58 | 2.32 |
| 211945 | Heath Sales (WI) | 2 | 13 | 5 | 56 | 2.63 |
| 211945 | Heath Sales 2 (WI) | 3 | 12 | 5 | 53 | 5.19 |
| FM658 | Heath Sales 2 (WI) | 3 | 12.5 | 3 | 50 | 3.44 |
| Labrador | Heath Sales 2 (WI) | 4 | 12 | 3 | 52 | 3.75 |
| Minuette | Kramer's | 4 | | 4 | 71 | 3.2 |
| 211945 | Kramer's | 3.5 | | 4 | 71 | 2.9 |
| Labrador | LeRoy (NY) | 3 | 13 | 3.5 | 55 | 2.3 |
| Minuette | LeRoy (NY) | 4 | 8.5 | 3.5 | 54 | 1.6 |
| FM658 | LeRoy (NY) | 2 | 13 | 3 | 53 | 2.7 |
| 211945 | LeRoy (NY) | 4 | 11 | 4.5 | 56 | 2.1 |
| 211945 | New Richmond (WI) | 4 | 13 | 4.5 | 58 | 2.12 |
| Minuette | New Richmond (WI) | 3 | 11 | 3.5 | 63 | 1.12 |
| FM658 | New Richmond (WI) | 3 | 14 | 2.5 | 59 | 3.5 |
| Labrador | New Richmond (WI) | 2.5 | 14 | 3.5 | 64 | 1.3 |
| 211945 | Salem (OR) | 3 | 10 | 4 | 69 | 3.1 |
| Minuette | Salem (OR) | 4 | 8 | 3.5 | 68 | 3.6 |
| Labrador | Sun Prairie (WI) | 4 | 12.5 | 3 | 56 | 3.1 |
| 211945 | Sun Prairie (WI) | 3 | 12 | 4.5 | | 1.8 |
| FM658 | Sun Prairie (WI) | 3 | 13 | 3.5 | 53 | 2.45 |

TABLE 2-continued

Overall Comparisons: Pod Characteristics
Garden Bean named '211945' vs Checks Year: 2001

| Variety | Location | Pod Position | Pod Length | Pod Color | Maturity | Yield |
|---|---|---|---|---|---|---|
| 211945 | Sun Prairie (WI) | 3 | 12 | 4.5 | | 1.6 |
| Labrador | Sun Prairie (WI) | 3.5 | 12 | 3 | 58 | 1.4 |
| FM658 | Sun Prairie (WI) | 3.5 | 12.5 | 3.5 | 59 | 1.65 |
| Minuette | Sun Prairie (WI) | 3.5 | 10 | 4 | 59 | 1.65 |
| Minuette | Sun Prairie (WI) | 3 | 10 | 3.5 | 58 | 2.1 |
| 211945 | Texas | 3 | 14 | 4.5 | 62 | 2.8 |
| Labrador | Texas | 2.5 | 13.5 | 4 | 62 | 0.5 |
| FM658 | Texas | 2 | 13 | 4 | 59 | 2.3 |

Table 3: Plant characteristics, data collected in 2000 in several locations.

The first column lists the variety tested.
The second column shows the location.
Column 3 shows the plant height in inches.
Column 4 shows the plant width in inches.
Column 5 shows the plants habit on a scale from 1 to 5, with 1 being prone, 3 being moderate, 4 being upright and 5 being erect.

TABLE 3

Overall Comparisons Plant characteristics
Garden Bean named '211945' vs Checks Year: 2000

| Variety | Location | Plant Height | Plant width | Plant Habit |
|---|---|---|---|---|
| Minuette | Delmarva (MD) | 22 | 18 | 4 |
| Minuette | Delmarva (MD) | 20.5 | 17 | 4 |
| Labrador | Delmarva (MD) | 23.6 | 18 | 3 |
| Labrador | Delmarva (MD) | 23.6 | 18 | 4 |
| 211945 | Delmarva (MD) | 20 | 16 | 4.5 |
| Minuette | Delmarva (MD) | 23 | 17 | 4 |
| Labrador | Delmarva (MD) | 19 | 15.5 | 3.5 |
| FM 658 | Delmarva (MD) | 19 | 17 | 3 |
| 211945 | Green Bay (WI) | 22 | 21 | 5 |
| Minuette | Green Bay (WI) | 14 | 17 | 2 |
| FM 658 | Green Bay (WI) | 20 | 18 | 4 |
| Labrador | Green Bay (WI) | 16 | 17 | 1 |
| 211945 | Havana (IL) | 13 | 14 | 4 |
| Labrador | Havana (IL) | 11 | 10 | 3 |
| FM 658 | Havana (IL) | 12 | 14 | 3 |
| 211945 | Heath (WI) | 18 | 19 | 4 |
| Labrador | Heath (WI) | 19 | 18 | 4 |
| FM 658 | Heath (WI) | 22 | 24 | 3.5 |
| Labrador | Heath (WI) | 24 | 23 | 4 |
| HMX 5591 | Heath (WI) | 20 | 18 | 4.5 |
| 211945 | Heath (WI) | 16 | 16 | 4 |
| FM 658 | Heath (WI) | 16 | 22 | 3.5 |
| HMX 5991 | Heath (WI) | 22 | 18 | 5 |
| 211945 | Kenyan (MN) | 16 | 16 | 4 |
| Minuette | Kenyan (MN) | 12 | 18 | 2 |
| FM 658 | Kenyan (MN) | 15 | 17 | 3 |
| Labrador | Kenyan (MN) | 16 | 18 | 2 |
| Labrador | LeRoy (NY) | 19.5 | 21 | 3.5 |
| Minuette | LeRoy (NY) | 17.8 | 19.5 | 3 |
| Labrador | LeRoy (NY) | 21 | 18.5 | 3.5 |
| 211945 | New Richmond (WI) | 14 | 13 | 4 |
| Labrador | New Richmond (WI) | 16 | 15 | 4 |
| FM 658 | New Richmond (WI) | 15 | 18 | 4 |
| Minuette | New Richmond (WI) | 14 | 15 | 4 |
| Minuette | New York | 18 | 21 | 3 |
| FM 658 | New York | 17 | 20 | 3 |
| Labrador | New York | 24 | 22 | 3.5 |
| 211945 | New York | 24 | 18.5 | 4.5 |

Table 4: Pods Characteristics, data Collected in 2000 in Several Locations.

The first column lists the variety tested.
The second column shows the location.
Column 3 shows the pods position on a scale from 1 to 5 with 1 being all pods on ground, 3 being pods just off the ground and 5 being pods high off the ground.
Column 4 shows the pods length in inches.
Column 5 shows the pod color on a scale from 1 to 5, 1 being lightly colored, 3 being medium, and 5 being dark.
Column 6 shows the maturity (optimum maturity in days)
Column 7 shows the yield in net pounds per 5 feet.

TABLE 4

Overall Comparisons Pod characteristics
Garden Bean named '211945' vs Checks Year: 2000

| Variety | Location | Pod Position | Pod length | Pod Color | Maturity | Yield |
|---|---|---|---|---|---|---|
| Minuette | Delmarva (MD) | 4 | 4.3 | 4 | 55 | 2.4 |
| Minuette | Delmarva (MD) | 3.5 | 4.3 | 4 | 59 | 2 |
| Labrador | Delmarva (MD) | 3 | 5 | 3.5 | 58 | 2.3 |
| Labrador | Delmarva (MD) | 3.5 | 5 | 3.5 | 54 | 1.8 |
| 211945 | Delmarva (MD) | 4 | 4.7 | 4 | 56 | 2.5 |
| Minuette | Delmarva (MD) | 4 | 4.7 | 4 | 56 | 2.4 |
| Labrador | Delmarva (MD) | 3.5 | 4.7 | 3.5 | 54 | 1.3 |
| FM 658 | Delmarva (MD) | 3.5 | 4.7 | 3.5 | 54 | 2.8 |
| 211945 | Green Bay (WI) | 4 | 5.7 | 3 | 62 | 2.56 |
| Minuette | Green Bay (WI) | 4 | 4.7 | 4 | 62 | 2.75 |
| FM 658 | Green Bay (WI) | 3 | 5 | 4 | 60 | 2.56 |
| Labrador | Green Bay (WI) | 3 | 5 | 4 | 63 | 1.44 |
| 211945 | Havana (IL) | 4 | 5 | 5 | 59 | 1.5 |
| Labrador | Havana (IL) | 3 | 5 | 4 | 59 | 1.19 |
| FM 658 | Havana (IL) | 2 | 5 | 4 | 57 | 1.5 |
| 211945 | Heath (WI) | 2 | | | | |
| Labrador | Heath (WI) | 3 | 5.5 | 3 | | 3.5 |
| FM 658 | Heath (WI) | 3 | 5.3 | 3 | | 5.2 |
| Labrador | Heath (WI) | 4 | 5 | 3.5 | | 3.5 |
| HMX 5591 | Heath (WI) | 5 | 4.3 | 4 | | 2.4 |
| 211945 | Heath (WI) | 2 | 5 | 4 | | 2.8 |
| FM 658 | Heath (WI) | 2 | 5 | 2.5 | | 4.7 |
| HMX 5991 | Heath (WI) | 5 | | | | |
| 211945 | Kenyan (MN) | 4 | 5.7 | 4 | 63 | 3.13 |
| Minuette | Kenyan (MN) | | | | | |
| FM 658 | Kenyan (MN) | 4 | 5.7 | 3.5 | 63 | 3.13 |
| Labrador | Kenyan (MN) | 3 | 5.5 | 3 | 62 | 3.35 |
| Labrador | LeRoy (NY) | 3.5 | 5.5 | 3.5 | 62 | 4.7 |
| Minuette | LeRoy (NY) | 3 | 5.5 | 4 | 61 | 4.2 |
| Labrador | LeRoy (NY) | 3.5 | 5.5 | 3.5 | 62 | 3.5 |
| 211945 | New Richmond (WI) | 4 | 5 | 5 | | 4.19 |
| Labrador | New Richmond (WI) | 3 | 4.5 | 4 | | 2.88 |
| FM 658 | New Richmond (WI) | 4 | 5 | 4 | | 3.69 |
| Minuette | New Richmond (WI) | 3 | 4.7 | 3 | | 3.25 |
| Minuette | New York | 3 | 5 | 4 | 66 | 3.6 |

TABLE 4-continued

Overall Comparisons Pod characteristics
Garden Bean named '211945' vs Checks Year: 2000

| Variety | Location | Pod Position | Pod length | Pod Color | Maturity | Yield |
|---|---|---|---|---|---|---|
| FM 658 | New York | 3 | 5 | 3 | 59 | 4.3 |
| Labrador | New York | 3.5 | 6.2 | 3.5 | 61 | 4.3 |
| 211945 | New York | 4.5 | 6.2 | 4 | 63 | 3.4 |

Deposit Information

A deposit of the Harris Moran Seed Company proprietary garden bean named '211945' disclosed above and recited in the appended claims has been made with National Collections of Industrial Food and Marine Bacteria (NCIMB), 23 St. Machar Drive, Aberdeen, Scotland, AB24 3RY, United Kingdom. The date of deposit was Nov. 26, 2004. The deposit of 2,500 seeds was taken from the same deposit maintained by Harris Moran Seed Company since prior to the filing date of this application. All restrictions upon the deposit have been removed and the deposit is intended to meet all of the requirements of 37 C.F.R. §1.801–1.809. The NCIMB accession number for garden bean named '211945' is NCIMB No. 41261. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding. However, it will be obvious that certain changes and modifications such as single gene modifications and mutations, somaclonal variants, variant individuals selected from large populations of the plants of the instant line and the like may be practiced within the scope of the invention, as limited only by the scope of the appended claims.

What is claimed is:

1. A Phaseolus vulgaris L. garden bean seed designated '211945', wherein a sample of said seed has been deposited under NCIMB No. 41261.

2. A plant, or a part thereof, produced by growing the seed of claim 1.

3. Pollen of the plant of claim 2.

4. An ovule of the plant of claim 2.

5. A tissue culture of regenerable cells of a bean plant of variety '211945', wherein the tissue regenerates plants having all the morphological and physiological characteristics of Phaseolus vulgaris L. bean line '211945', representative seeds having been deposited under NCIMB No. 41261.

6. The tissue culture of claim 5, selected from the group consisting of protoplast and calli, wherein the regenerable cells are produced from embryo, meristematic cells, leaves, pollen, embryo, root, root tips, stems, anther, flowers, seeds or pods.

7. A Phaseolus vulgaris L. garden bean plant regenerated from the tissue culture of claim 5, wherein the regenerated plant has all the morphological and physiological characteristics of Phaseolus vulgaris L. bean plant '211945', representative seeds having been deposited under NCIMB No. 41261.

8. A method for producing a hybrid garden bean seed comprising crossing a first parent garden bean plant with a second parent garden bean plant and harvesting the resultant hybrid garden bean seed, wherein said first or second parent garden bean plant is the Phaseolus vulgaris L. garden bean plant of claim 2.

9. A method of producing an herbicide resistant bean plant comprising transforming the bean plant of claim 2 with a transgene that confers herbicide resistance.

10. An herbicide resistant bean plant produced by the method of claim 9.

11. The bean plant of claim 10, wherein the transgene confers resistance to an herbicide selected from the group consisting of imidazolinone, sulfonvlurea, glyphosate, glufosinate, L-phosohinothricin, triazine and benzonitrile.

12. A method of producing an insect resistant bean plant comprising transforming the bean plant of claim 2 with a transgene that confers insect resistance.

13. An insect resistant bean plant produced by the method of claim 12.

14. The bean plant of claim 13, wherein the transgene encodes a Bacillus thuringiensis protein.

15. A method of producing a disease resistant bean plant comprising transforming the bean plant of claim 2 with a transgene that confers resistance to bacterial, fungal or viral disease.

16. A disease resistant bean plant produced by the method of claim 15.

* * * * *